United States Patent [19]

Saito et al.

[11] 4,218,398

[45] Aug. 19, 1980

[54] PROCESS FOR PRODUCING DIMETHYLFORMAMIDE

[75] Inventors: Masao Saito; Kinichi Mizuno; Yuzi Onda; Tetsuo Aoyama; Kumiko Kato, all of Niigata, Japan

[73] Assignee: Mitsubishi Gas Chemical Company, Inc., Tokyo, Japan

[21] Appl. No.: 972,257

[22] Filed: Dec. 22, 1978

Related U.S. Application Data

[63] Continuation of Ser. No. 844,077, Oct. 20, 1977, abandoned.

[30] Foreign Application Priority Data

Nov. 1, 1976 [JP] Japan .................................. 51-131527

[51] Int. Cl.² ............................................. C07C 103/36
[52] U.S. Cl. ............................. 260/561 R; 260/562 R
[58] Field of Search ........................ 260/561 R, 562 R

[56] References Cited

U.S. PATENT DOCUMENTS

| | | | |
|---|---|---|---|
| 2,677,706 | 5/1954 | Giachinu | 260/561 R |
| 3,099,689 | 7/1963 | Cragg | 260/562 R |
| 3,530,182 | 9/1970 | Haynes | 260/561 R |

FOREIGN PATENT DOCUMENTS

| | | | |
|---|---|---|---|
| 863800 | 1/1953 | Fed. Rep. of Germany | 260/561 R |
| 397852 | 8/1933 | United Kingdom | 252/441 |

OTHER PUBLICATIONS

Aliev et al., Chem. Abstracts 57 (1962), 8413f.
Beckwith, The Chemistry of Amides, Interscience Publishers N.Y., N.Y. 1970, p. 118.

*Primary Examiner*—Arthur P. Demers
*Attorney, Agent, or Firm*—Armstrong, Nikaido, Marmelstein & Kubovcik

[57] ABSTRACT

Dimethylformamide mg.produced by reaction of monomethylamine and trimethylamine at a molar ratio of trimethylamine to monomethylamine of 0.1–10, with carbon monoxide in the presence of 1–500 mg. atom of at least one of iodine, bromine, iodides and bromides as a catalyst in term of halogen per one mole of raw material methylamines at a temperature of 100°–350° C. under a pressure of at least 50 kg/cm² gage. Dimethylformamide is produced in a very high yield with a high selectivity from monomethylamine and trimethylamine having less demand among three species of methylamines formed from methanol and ammonia.

4 Claims, No Drawings

PROCESS FOR PRODUCING DIMETHYLFORMAMIDE

This is a continuation of application Ser. No. 844,077, filed Oct. 20, 1977, now abandoned.

This invention relates to a process for producing dimethylformamide which comprises making monomethylamine and trimethylamine react with carbon monoxide in the presence of at least one of iodine, bromine, iodides and bromides as a catalyst.

Generally, dimethylformamide is produced by reaction of dimethylamine with carbon monoxide or methyl formate (Kirk-Othmer: Encyclopedia of Chemical Technology, Second Edition, Vol. 10, pages 109–110, Interscience Publishers, New York). Dimethylamine used as the raw material in said prior art is usually prepared by dehydration reaction of methyl alcohol and ammonia, but a large amount of monomethylamine and trimethylamine is inevitably by-produced in addition to dimethylamine. Commercial demands for monomethylamine and trimethylamine are however poor, as compared with that of dimethylamine, and thus most of these two methylamines is usually recycled to methylamine synthesis system, where they are converted to dimethylamine. That is, if monomethylamine and trimethylamine having the less demands can be used as the raw material for dimethylformamide in place of dimethylamine, such will bring about a remarkable rationalization to the methylamine production industry with a great commercial significance.

To meet such a desire, U.S. Pat. No. 2,677,706 discloses a process based on reaction of monomethylamine and/or dimethylamine, or further together with trimethylamine, with carbon monoxide in the presence of cuprous chloride, cupric chloride, potassium acetate, boron trifluoride or ammonium chloride as a catalyst, but selectivities of monomethylamine and trimethylamine to dimethylformamide are so low that the prior art process is not satisfactory as a commercial process.

The present inventors invented, on a previous occasion, a process for producing methylformamide by reaction of monomethylformamide and trimethylamine with carbon monoxide, and filed a patent application (U.S. Patent Application Ser. No. 802,524). Monomethylformamide is readily obtained by reaction of monomethylamine with carbon monoxide in the presence of alkali metal alcoholate as a catalyst or methyl formate, and consequently dimethylformamide can be obtained from monomethylamine and trimethylamine by successively conducting at two reactions, but the process must be carried out at two stages. This is the disadvantage of the prior invention.

As a result of further extensive studies of the process for producing dimethylformamide from monomethylamine or trimethylamine as the raw material, the present inventors have found a novel process for producing dimethylformamide in high yield by reaction of monomethylamine and trimethylamine with carbon monoxide in the presence of at least one of iodine, bromine, iodides and bromides as a catalyst.

Examples of the effective catalysts used in the present invention include iodine, bromine, ammonium iodide, ammonium bromide, iodides and bromides of such metals as copper, zinc, magnesium, calcium, strontium, barium, iron, cobalt, nickel, ruthenium, rhodium, palladium, etc., hydroiodic acid, hydrobromic acid, alkyl iodides, alkyl bromides, etc. These catalysts can be used alone, or in a combination of at least two thereof.

An appropriate amount of the catalyst to be used as 1–500 mg·atom, preferably 5–300 mg·atom in terms of halogen per mole of raw material methylamines. When the amount of the catalyst to be used is below 1 mg·atom, the yield becomes lower, whereas the amount of the catalyst above 500 mg·atom is not practical.

An appropriate molar ratio of trimethylamine to monomethylamine to be used is 0.1–10, preferably 0.5–5. The molar ratio outside of said range of 0.1–10 is not practical, because the amount of unreacted materials is increased.

The amount of monomethylformamide formed is increased in a relatively low ratio even in said range, but according to the study made by the present inventors, it is possible to recycle said monomethylformamide to the reaction system, because said monomethylformamide reacts with trimethylamine and carbon monoxide to form dimethylformamide. In that case, the recycled monomethylformamide can act as a solvent at the initial stage of reaction. In that case, a molar ratio of timethylamine to sum total of monomethylformamide and monomethylamine must be adjusted to said range of the molar ratio of trimethylamine to monomethylamine.

The reaction is carried out under a pressure of at least 50 kg/cm² gage, preferably 100–800 kg/cm² gage. Unfavorably, side reaction is promoted under a pressure below 50 kg/cm² gage, whereas much higher pressure is not practical in view of economy, though applicable from the viewpoint of reaction. Carbon monoxide is the raw material, and also serves to maintain the reaction pressure at the same time. Thus, carbon monoxide is used in a large excess, but a gas mixture of carbon monoxide with nitrogen gas can be used, as long as the gas mixture has a partial pressure of carbon monoxide of at least 10 kg/cm² gage.

Reaction is also carried out at a temperature of 100°–350° C., preferably 150°–300° C. A temperature outside said range of 100°–350° C. should not be used in view of reaction rate and selectivity.

In the present invention, it is not essential to use the so-called solvent, but addition of a small amount of a solvent can make a liquid phase portion present even at the initial stage of reaction at a temperature above the critical temperature of the raw material methylamines, permitting a temperature control to be easily controlled. Examples of applicable solvents include solvents of amide system such as dimethylformamide, N-methylpyrrolidone, etc., saturated aliphatic hydrocarbons such as hexane, heptane, octane, etc., and aromatic hydrocarbons such as benzene, toluene, xylene, etc.

It is presumed that a main reaction takes place according to the following equation in the present invention, so long as the equation is expressed in a relation to the raw materials and the product.

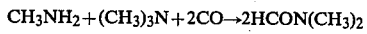

$$CH_3NH_2 + (CH_3)_3N + 2CO \rightarrow 2HCON(CH_3)_2$$

However, it has not been confirmed yet what reactions take place in the process from these raw materials to the product, and it seems that reactions failing to meet said equation probably take place.

According to the study made by the present inventors, the present catalyst is also effective for reaction to form dimethylformamide from dimethylamine and carbon monoxide, and thus a contamination of the reaction system with dimethylamine is not objectionable.

In the present invention, dimethylformamide can be obtained in a high yield with a high selectivity. Furthermore, both monomethylamine and trimethylamine having less demand among three species of methylamines formed from methanol and ammonia can be effectively utilized for the production of dimethylformamide. Thus, the present invention can provide a very important commercial significance.

The present invention will be described below in detail, referring to Examples and Comparative Examples.

EXAMPLE 1

216.4 m moles of monomethylamine, 176.1 m mole of trimethylamine, and 15.7 mg·atoms of iodine as a catalyst dissolved in 6.75 g of N-methylpyrrolidone were charged into a 100-ml autoclave and subjected to reaction at a temperature of 260° C. under a pressure of 250 kg/cm$^2$ gage attained by carbon monoxide for 4 hours. The resulting product was analyzed by gas chromatography, and it was found that 227.4 m moles of dimethylformamide was formed.

EXAMPLE 2

216.5 m moles of monomethylamine, 178.2 m moles of trimethylamine and 16.1 mg·atom of iodine as a catalyst were charged into an autoclave, and subjected to reaction at a temperature of 258° C. under a pressure of 250 kg/cm$^2$ gage attained by carbon monoxide. As a result of analysis of the product, it was found that 220.8 m moles of dimethylformamide was formed.

EXAMPLES 3-22 AND COMPARATIVE EXAMPLES 1 AND 2

Results obtained by changing molar ratio of the raw materials, species and amounts of catalyst, temperature, pressure, etc. to varied degrees are shown in Table, together with the results of Examples 1 and 2. The reactor used was an autoclave having a capacity of 100 ml in every case.

Comparative Examples 1 and 2 are cases using ammonium chloride disclosed in U.S. Pat. No. 2,677,706 as a catalyst.

Table

| Example No. | 1 | 2 | 3 | 4 | 5 | 6 | 7 | 8 |
|---|---|---|---|---|---|---|---|---|
| Catalyst | I$_2$ | I$_2$ | CuI | MgI | CoI$_2$ | PdI$_2$ | CH$_3$I | NH$_4$Br |
| Catalyst amount in terms of halogen (mg . atom) | 15.7 | 16.1 | 16.1 | 16.1 | 16.6 | 16.1 | 16.6 | 16.1 |
| Catalyst ratio in terms of halogen (mg . atom/total amine) | 40.0 | 40.8 | 48.3 | 45.4 | 41.9 | 46.1 | 42.2 | 41.3 |
| Monomethylamine (m mole) | 216.4 | 216.5 | 159.3 | 178.2 | 216.7 | 172.6 | 220.0 | 218.7 |
| Trimethylamine (m mole) | 176.1 | 178.2 | 174.0 | 176.1 | 179.2 | 176.5 | 173.1 | 171.1 |
| Trimethylamine/monomethylamine (by mole) | 0.814 | 0.823 | 1.092 | 0.988 | 0.827 | 1.023 | 0.787 | 0.782 |
| Reaction pressure (kg/cm gage) | 250 | 250 | 250 | 250 | 250 | 250 | 250 | 250 |
| Reaction temperature (°C.) | 260 | 258 | 258 | 258 | 257 | 256 | 258 | 257 |
| Reaction time (hr) | 4 | 4 | 4 | 4 | 4 | 4 | 4 | 4 |
| Monomethylformamide yield (m moles) | 52.2 | 50.9 | 46.0 | 54.2 | 56.2 | 48.2 | 49.1 | 40.5 |
| Dimethylformamide yield (m moles) | 227.4 | 220.8 | 176.8 | 161.1 | 241.5 | 198.4 | 214.3 | 177.1 |
| Dimethylformamide yield per total methylamine (%) | 57.9 | 55.9 | 53.0 | 45.5 | 61.0 | 56.8 | 54.5 | 45.4 |
| Solvent | N-methyl-pyrrolidone 6.75 g | none | none | N-methyl-pyrrolidone 6.75 g | none | none | N-methyl-pyrrolidone 6.75 g | N-methyl-pyrrolidone 6.75 g |

| Example No. | 9 | 10 | 11 | 12 | 13 | 14 | 15 | 16 |
|---|---|---|---|---|---|---|---|---|
| Catalyst | NH$_4$I | Aqueous 57% HI solution | Br$_2$ | CoBr$_2$ | CH$_3$Br | NH$_4$I | NH$_4$I | NH$_4$I |
| Catalyst amount in terms of halogen (mg . atom) | 16.6 | 16.6 | 16.6 | 16.6 | 16.6 | 16.6 | 24.5 | 24.8 |
| Catalyst ratio in terms of halogen (mg . atom/total amine) | 42.2 | 42.4 | 42.3 | 41.7 | 42.7 | 41.5 | 62.9 | 63.2 |
| Monomethylamine (m mole) | 220.2 | 215.6 | 216.0 | 220.0 | 217.1 | 264.0 | 67.1 | 219.6 |
| Trimethylamine (m mole) | 173.4 | 176.2 | 176.6 | 178.3 | 171.5 | 136.4 | 322.1 | 173.1 |
| Trimethylamine/monomethylamine (by mole) | 0.787 | 0.817 | 0.818 | 0.810 | 0.790 | 0.517 | 4.800 | 0.788 |
| Reaction pressure | | | | | | | | |

| | | | | | | | | |
|---|---|---|---|---|---|---|---|---|
| (kg/cm gage) | 250 | 250 | 250 | 250 | 250 | 250 | 300 | 250 |
| Reaction temperature (°C.) | 257 | 258 | 258 | 258 | 258 | 259 | 268 | 258 |
| Reaction time (hr) | 4 | 4 | 4 | 4 | 4 | 4 | 4 | 4 |
| Monomethylformamide yield (m moles) | 48.8 | 50.2 | 47.1 | 51.0 | 45.9 | 71.3 | 2.3 | 58.5 |
| Dimethylformamide yield (m moles) | 212.1 | 217.8 | 187.2 | 230.2 | 187.7 | 197.6 | 133.3 | 252.3 |
| Dimethylformamide yield per total methylamine (%) | 53.9 | 55.6 | 47.7 | 57.8 | 48.3 | 49.4 | 34.2 | 64.2 |
| Solvent | N-methylpyrrolidone 6.75 g | none | none | none | none | N-methylpyrrolidone 6.75 g | N-methylpyrrolidone 6.75 g | N-methylpyrrolidone 6.75 g |

| Example No. | 17 | 18 | 19 | 20 | 21 | 22 | Comp. Ex. 1 | Comp. Ex. 2 |
|---|---|---|---|---|---|---|---|---|
| Catalyst | NH₄I | NH₄I | NH₄I | NH₄I | NH₄I | NH₄I | NH₄Cl | NH₄Cl |
| Catalyst amount in terms of halogen (mg . atom) | 2.9 | 91.8 | 54.8 | 24.8 | 54.8 | 24.8 | 15.1 | 22.4 |
| Catalyst ratio in terms of halogen (mg . atom/total amine) | 8.2 | 231.4 | 151.1 | 63.1 | 145.2 | 64.6 | 40.4 | 57.8 |
| Monomethylamine (m mole) | 172.6 | 217.2 | 180.7 | 219.7 | 189.0 | 204.5 | 204.4 | 215.4 |
| Trimethylamine (m mole) | 181.8 | 179.5 | 182.0 | 173.2 | 188.3 | 179.2 | 169.5 | 172.1 |
| Trimethylamine/monomethylamine (by mole) | 1.053 | 0.826 | 1.007 | 0.788 | 0.996 | 0.876 | 0.829 | 0.799 |
| Reaction pressure (kg/cm gage) | 400 | 250 | 300 | 250 | 100 | 600 | 250 | 250 |
| Reaction temperature (°C.) | 280 | 259 | 160 | 283 | 269 | 258 | 252 | 253 |
| Reaction time (hr) | 4 | 4 | 8 | 4 | 4 | 4 | 4 | 4 |
| Monomethylformamide yield (m moles) | 28.7 | 40.1 | 84.9 | 14.5 | 15.8 | 58.7 | 39.6 | 45.7 |
| Dimethylformamide yield (m moles) | 150.6 | 317.0 | 152.0 | 318.6 | 181.1 | 298.3 | 105.5 | 122.2 |
| Dimethylformamide yield per total methylamine (%) | 42.5 | 79.9 | 41.9 | 81.1 | 48.0 | 77.7 | 28.2 | 31.5 |
| Solvent | N-methylpyrrolidone 6.75 g | N-methylpyrrolidone 6.75 g | N-methylpyrrolidone 6.75 g | N-methylpyrrolidone 6.75 g | N-methylpyrrolidone 6.75 g | N-methylpyrrolidone 6.75 g | N-methylpyrrolidone 6.75 g | N-methylpyrrolidone 6.75 g |

What is claimed is:

1. A process for producing dimethylformamide which comprises reacting a mixture of monomethylamine and trimethylamine with carbon monoxide at a temperature of from 150°-300° C. in the presence of at least one catalyst selected from the group consisting of iodine; bromine; ammonium iodide; ammonium bromide; iodides and bromides of copper, zinc, magnesium, calcium, strontium, barium, iron, cobalt, nickel, ruthenium, rhodium and palladium; hydroidic acid; hydrobromic acid; alkyl iodides and alkyl bromides, the amount of said catalyst being 1-500 mg·atom in terms of halogen per mole of raw material amine mixture.

2. A process according to claim 1, wherein a molar ratio of trimethylamine to monomethylamine is 0.1-10.

3. A process according to claim 1, wherein the reaction is carried out under a pressure of at least 50 kg/cm² gage.

4. A process according to claim 3, wherein a carbon monoxide partial pressure is at least 10 kg/cm² gage.

* * * * *